United States Patent
Takimura

(10) Patent No.: US 9,456,753 B2
(45) Date of Patent: Oct. 4, 2016

(54) PROBE

(75) Inventor: Toshinori Takimura, Hachioji (JP)

(73) Assignee: Konica Minolta, Inc., Tokyo (JP)

( * ) Notice: Subject to any disclaimer, the term of this patent is extended or adjusted under 35 U.S.C. 154(b) by 583 days.

(21) Appl. No.: 13/995,097

(22) PCT Filed: Dec. 14, 2011

(86) PCT No.: PCT/JP2011/078865
§ 371 (c)(1),
(2), (4) Date: Jun. 17, 2013

(87) PCT Pub. No.: WO2012/081599
PCT Pub. Date: Jun. 21, 2012

(65) Prior Publication Data
US 2013/0267857 A1    Oct. 10, 2013

(30) Foreign Application Priority Data

Dec. 16, 2010 (JP) .................................. 2010-280557

(51) Int. Cl.
*A61B 5/00* (2006.01)
*G01N 21/64* (2006.01)

(52) U.S. Cl.
CPC .......... *A61B 5/0084* (2013.01); *A61B 5/0059* (2013.01); *A61B 5/0071* (2013.01); *G01N 21/645* (2013.01); *G01N 2021/6484* (2013.01)

(58) Field of Classification Search
None
See application file for complete search history.

(56) References Cited

U.S. PATENT DOCUMENTS

| | | | | | |
|---|---|---|---|---|---|
| 4,357,104 | A | * | 11/1982 | Davinson | G01B 11/14 250/559.38 |
| 6,023,367 | A | * | 2/2000 | Kurtz | F21V 5/04 348/E5.049 |
| 7,347,631 | B2 | * | 3/2008 | Suzuki | G02B 6/4204 385/15 |
| 8,942,523 | B2 | * | 1/2015 | Jono | A61B 5/0071 385/117 |
| 2006/0015014 | A1 | * | 1/2006 | Remijan | A61B 1/00135 600/182 |

FOREIGN PATENT DOCUMENTS

| | | |
|---|---|---|
| JP | 10-62653 | 3/1998 |
| JP | 2001-174712 | 6/2001 |
| JP | 2004-317437 | 11/2004 |
| JP | 2005-522293 | 7/2005 |
| JP | 2008-197241 | 8/2008 |
| JP | 2010-51606 | 3/2010 |
| JP | 2010-88665 | 4/2010 |
| WO | WO 02/071115 | 9/2002 |
| WO | WO 03/087793 | 10/2003 |

* cited by examiner

*Primary Examiner* — Long V Le
*Assistant Examiner* — Bradley Impink
(74) *Attorney, Agent, or Firm* — Cozen O'Connor

(57) ABSTRACT

Probe with a light-receiving optical fiber having an entrance face on the tip orthogonal to first optical axis; a light-emitting optical fiber having an exit face on the tip that is orthogonal to a second optical axis; and a lens with a positive refractive power that projects light exiting from the exit face onto the measurement site of a living tissue and focuses light radiated from the measurement site of the living tissue onto the entrance face. Lens has convex surface facing the entrance face and exit face, a flat surface formed on the side opposite the convex surface, and a third optical axis. Distance from center of convex surface to first optical axis of optical fiber is shorter than distance from center to second optical axis of optical fiber.

5 Claims, 8 Drawing Sheets

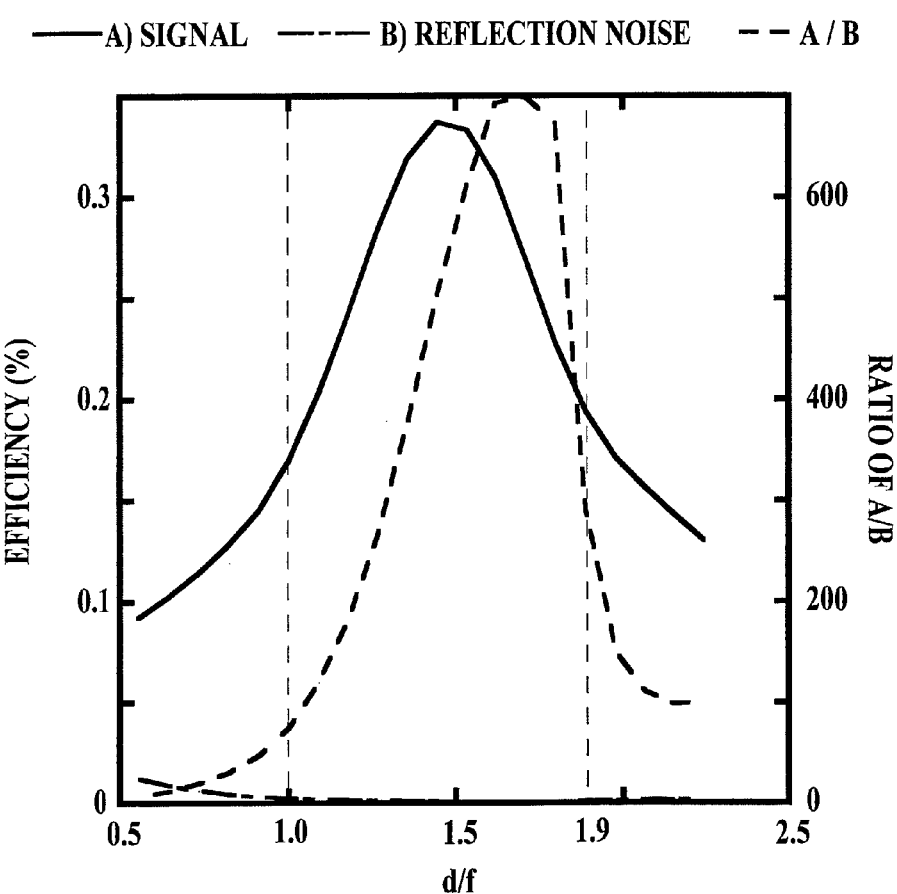

PROBE

RELATED APPLICATIONS

This is a U.S. national stage of International application No. PCT/JP2011/078865 filed on Dec. 14, 2011.

This patent application claims the priority of Japanese application no. 2010-280557 filed Dec. 16, 2010, the disclosure content of which is hereby incorporated by reference.

TECHNICAL FIELD

The present invention relates to a probe provided with an illuminating optical fiber, a receiving optical fiber and a lens.

BACKGROUND ART

Various techniques have been proposed and put into practical use for the purpose of observation and detection of lesional states of biological tissues. In particular, endoscope which is inserted into internal hollow organs, captures images of biological tissues and transmits the acquired images has widely been disseminated. The techniques having been proposed are directed not only to image diagnosis merely based on visible light, but also to techniques with wise use of ultrasonic wave, florescence or spectral light. In particular, the method making use of fluorescence takes an advantage of capability of real-time diagnosis.

In the fluorescence-assisted diagnosis, an excitation light is illuminated on a site of measurement so as to induce therefrom emission of fluorescence, and wavelength and intensity of the emitted fluorescence are analyzed. Probe has been developed for the convenience of such diagnosis, and has been used for diagnosing lesional states of biological tissues and status of disease of cancer and so forth (types of disease, range of invasion, etc.).

This sort of probe incorporates an illuminating optical fiber, a receiving optical fiber and a lens. Excitation light output from the end of the illuminating optical fiber is cast onto a site to be measured of a biological tissue, and the fluorescence emitted from the site to be measured of the biological tissue is cast through the lens onto to the end of the receiving optical fiber.

Patent Document 1 discloses a technique of immobilizing two optical fibers to a ferrule, but with no disclosure on immobilization of the lens.

Patent Document 2 discloses a technique of disposing a coupling lens ahead of the end faces of two optical fibers, with one optical fiber aligned with the axis of a ferrule, the other optical fiber decentered from the axis of the ferrule, the end faces of these two optical fibers and the ferrule are aligned, and these end faces are inclined with respect to the optical axis of the optical fiber.

Patent Document 3 discloses a technique of disposing a plurality of lenses between one multi-mode optical fiber and an LED, so as to condense light emitted from the LED through the plurality of lenses onto the end of the multi-mode optical fiber.

PRIOR ART DOCUMENTS

Patent Documents

Patent Document 1: Japanese Patent Application Laid Open Publication No. H10-62653

Patent Document 2: International Publication WO2002/071115

Patent Document 3: Japanese Patent Application Laid Open Publication No. 2008-197241

SUMMARY OF THE INVENTION

Problems to be Solved by the Invention

None of the techniques of Patent Documents 1 to 3 has, however, discloses an optimum positional relation between the lens and the optical fibers. More specifically, these techniques have not been directed to reduce noise possibly produced when fluorescence emitted from the site of measurement of the biological tissue reflects, for example, on the surface of the lens.

It is therefore an object of the present invention to allow light emitted from a site of measurement of a biological tissue to efficiently enter the end of the receiving optical fiber, and to reduce reflection noise typically on the surface of the lens.

Means for Solving the Problem

In order to solve the above problem, a probe includes a receiving optical fiber having a first optical axis and having at an end thereof an input face orthogonal to the first optical axis, an illuminating optical fiber having a second optical axis parallel to the first optical axis and having at an end thereof an output face orthogonal to the second optical axis and a lens having a positive power, which casts light output from the output face of the illuminating optical fiber onto a site of measurement of a biological tissue, and condenses light emitted from the site of measurement of the biological tissue onto the input face of the receiving optical fiber, and the lens includes a convex surface faced to the input face and the output face, a flat surface formed opposite to the convex surface, and a third optical axis which crosses the convex surface at the center thereof and orthogonally crosses the flat surface at the center thereof, and the distance from the center of the convex surface to the first optical axis is shorter than the distance from the center of the convex surface to the second optical axis.

Preferably, the first optical axis, the second optical axis and the third optical axis are in parallel to each other.

Preferably, assuming a numerical aperture of the output face of the illuminating optical fiber as NA, an effective diameter of the lens as $\phi$, a distance from the center of the convex surface of the lens to the input face of the receiving optical fiber and to the output face of the illuminating optical fiber as d, and the distance from the center of the convex surface to the second optical axis as L2, the relation below is satisfied:

$$0 < |L2| \leq \frac{\varphi}{2} - d \times \tan(\sin^{-1} NA). \quad \text{[Mathematical Formula 1]}$$

Preferably, the third optical axis and the first optical axis are aligned.

Preferably, the third optical axis is inclined away from the first optical axis.

Preferably, assuming an angle of inclination of the third optical axis away from the first optical axis as $\theta$, the numerical aperture of the output face of the illuminating optical fiber as NA, the effective diameter of the lens as $\phi$, the distance from the center of the convex surface of the lens to the input face of the receiving optical fiber and the output face of the illuminating optical fiber as d, and the distance from the center of the convex surface to the second optical axis as L2, the relation below is satisfied:

$$0 < |L2| \leq (\sin\theta + \cos\theta)\frac{\varphi}{2} - d \times \tan(\sin^{-1} NA).$$ [Mathematical Formula 2]

Advantageous Effects of Invention

According to the present invention, light emitted from the site of measurement of the biological tissue may efficiently enter the input face of the receiving optical fiber.

It is now also enabled to reduce noise caused by reflection of light typically on the surface of the lens.

BRIEF DESCRIPTION OF DRAWINGS

FIG. 8 This is a graph illustrating efficiency of incidence of light, efficiency of reflection noise and SN ratio in the probe illustrated in FIG. 5A.

EMBODIMENTS FOR CARRYING OUT THE INVENTION

Modes of carrying out the present invention will be explained below, referring to the attached drawings. Note that any technical limitations made in the description below, preferable for embodying the present invention, are not intended to limit the scope of the present invention to the embodiment and illustrated examples.

First Embodiment

Figure 1:
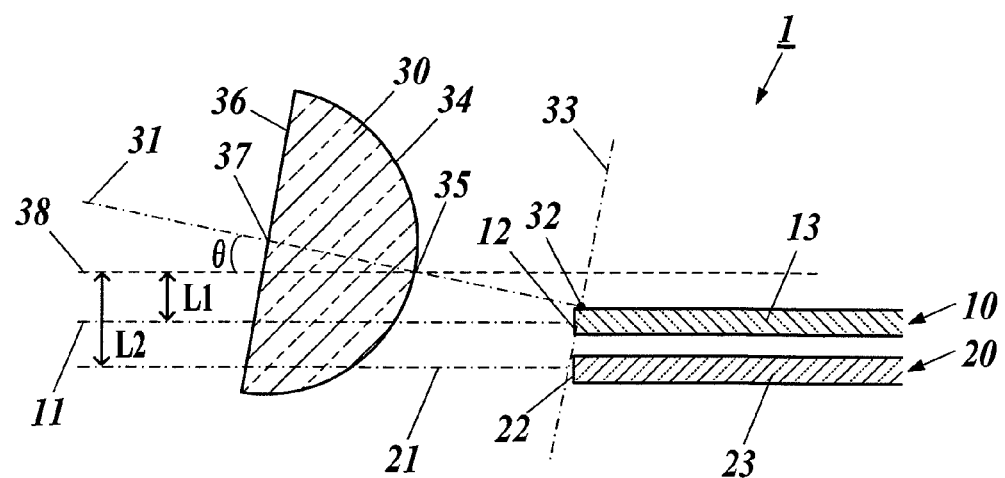
FIG. 1 This is a schematic cross sectional view illustrating a near-end portion of a probe according to a first embodiment of the present invention.

FIG. 1 is a sectional view illustrating a near-end portion of a probe 1.

The probe 1 has an illuminating optical fiber 20, a receiving optical fiber 10 and a lens 30.

The base end portion of the probe 1 is connected to an unillustrated base unit. The base units has a light source of excitation light, a spectrometer, an analyzer and so forth. The base end of the illuminating optical fiber 20 is connected to the light source, and the base end of the receiving optical fiber 10 is connected to the spectrometer. The excitation light (X-ray, ultraviolet radiation, visible light, electromagnetic wave, etc.) emitted from the light source enters the base end of the illuminating optical fiber 20, propagates inside the illuminating optical fiber 20 to reach the end thereof, and output from the end thereof. The excitation light output from the end of the illuminating optical fiber 20 is then cast on a site of measurement through the lens 30. The site of measurement of the biological body is excited by the excitation light, and generates fluorescence. The fluorescence generated from the site of measurement of the biological tissue is condensed by the lens 30 onto the end of the receiving optical fiber 10, and enters the end. The fluorescence entered the receiving optical fiber 10 propagates therein to reach the base end of the receiving optical fiber 10, and is then input to the spectrometer.

The receiving optical fiber 10 has a first optical axis (centerline) 11 which extends along the receiving optical fiber 10. The illuminating optical fiber 20 has a second optical axis (center line) 21 which extends along the illuminating optical fiber 20. A near-end portion 13 of the receiving optical fiber 10 and a near-end portion 23 of the illuminating optical fiber 20 are immobilized to an unillustrated ferrule, and thereby the first optical axis 11 of the near-end portion 13 of the receiving optical fiber 10 is disposed in parallel with the second optical axis 21 of the near-end portion 23 of the illuminating optical fiber 20. By the ferrule, the near-end portion 13 of the receiving optical fiber 10 and the near-end portion 23 of the illuminating optical fiber 20 are prevented from being bent.

The near-end portion 13 of the receiving optical fiber 10 and the near-end portion 23 of the illuminating optical fiber 20 are arranged so as to be adjacent to each other. The near-end portion 13 of the receiving optical fiber 10 and the near-end portion 23 of the illuminating optical fiber 20 may be brought into contact or may be slightly spaced.

The receiving optical fiber 10 has the input face 12 formed at the end thereof. The first optical axis 11 of the receiving optical fiber 10 orthogonally crosses the input face 12 at the center thereof.

The illuminating optical fiber 20 has the output face 22 formed at the end thereof. The second optical axis 21 of the illuminating optical fiber 20 orthogonally crosses the output face 22 at the center thereof.

The input face 12 and the output face 22 expose without being covered with the ferrule. The input face 12 and the output face 22 are aligned. While the input face 12 and the output face 22 may be shifted back and forth (in the direction of the first optical axis 11 and the second optical axis 21), the input face 12 and the output face 22 are anyway in a close vicinity.

The core diameter of the receiving optical fiber 10 and the core diameter of the illuminating optical fiber 20 may be same or different.

The lens 30 is disposed ahead of the input face 12 of the receiving optical fiber 10 and ahead of the output face 22 of the illuminating optical fiber 20. The lens 30 is fixed by a holder, and the holder is attached to the ferrule. The relative positional relation among the near-end portion 13 of the receiving optical fiber 10, the near-end portion 23 of the illuminating optical fiber 20, and the lens 30 is kept unchanged.

The lens 30 has a third optical axis (center line) 31. The lens 30 has a fiber-opposing face 34 on the rear side (on the side of the optical fibers 10, 20), and has an object-opposing face 36 on the front side (object side).

The lens 30 is a plano-convex lens. More specifically, the fiber-opposing face 34 is configured by a convex surface, and the object-opposing face 36 is configured by a flat surface. The fiber-opposing face 34 is preferably configured by a spherical convex surface, and more preferably a semispherical convex face. Note that the fiber-opposing face 34 may be configured by an aspherical convex surface.

The third optical axis 31 is an axis of rotation symmetry, and the fiber-opposing face 34 and the object-opposing face 36 are surfaces rotationally symmetrical around the third optical axis 31. The third optical axis 31 crosses the fiber-opposing face 34 at right angles at the center 35 thereof (nodal point on the fiber side). The third optical axis 31 crosses the object-opposing face 36 at right angles at the center 37 thereof (nodal point at the object side).

The lens 30 has a positive power. A focal point 32 of the lens 30 is set on the third optical axis 31 and behind the fiber-opposing face 34. A plane which includes the focal point and crosses the third optical axis 31 at right angles is a focal plane 33. The focal point 32 of the lens 30 is preferably set on the input face 12 of the receiving optical fiber 10, or in the vicinity thereof. The focal point 32 of the lens 30 is also preferably set on the output face 22 of the illuminating optical fiber 20, or in the vicinity thereof.

The lens 30 is disposed so as to oppose the fiber-opposing face 34 thereof to the input face 12 of the receiving optical fiber 10 and the output face 22 of the illuminating optical fiber 20. The object-opposing face 36 is opposed to the site of measurement of the biological tissue.

The third optical axis 31 of the lens 30, the first optical axis 11 of the receiving optical fiber 10, and the second optical axis 21 of the illuminating optical fiber 20 are aligned on the same plane. The cross section shown in FIG. 1 is taken along a plane which contain all of the third optical axis 31 of the lens 30, the first optical axis 11 of the receiving optical fiber 10, and the second optical axis 21 of the illuminating optical fiber 20.

It is preferable that both of the first optical axis 11 of the receiving optical fiber 10 and the second optical axis 21 of the illuminating optical fiber 20 cross the fiber-opposing face 34 of the lens 30. Alternatively, the first optical axis 11 of the receiving optical fiber 10 may cross the fiber-opposing face 34 of the lens 30, whereas the second optical axis 21 of the illuminating optical fiber 20 does not have to cross the fiber-opposing face 34 of the lens 30.

It is preferable that both of the first optical axis 11 of the receiving optical fiber 10 and the second optical axis 21 of the illuminating optical fiber 20 cross the object-opposing face 36 of the lens 30. Alternatively, the first optical axis 11 of the receiving optical fiber 10 may cross the object-opposing face 36 of the lens 30, and the second optical axis 21 of the illuminating optical fiber 20 does not have to cross the object-opposing face 36 of the lens 30.

The second optical axis 21 of the illuminating optical fiber 20 is more distant away from the center 35 of the fiber-opposing face 34 than the first optical axis 11 of the receiving optical fiber 10 is. More specifically, assuming now that the distance from the center 35 of the fiber-opposing face 34 to the first optical axis 11 of the receiving optical fiber 10 as L1, and the distance from the center 35 of the fiber-opposing face 34 to the second optical axis 21 of the illuminating optical fiber 20 as L2, the relation (1) below is satisfied:

$$L1 < L2 \quad (1)$$

A reference line 38 illustrated in FIG. 1 contains the center 35 of the fiber opposing face 34 and is parallel to the first optical axis 11 of the receiving optical fiber 10 and the second optical axis 21 of the illuminating optical fiber 20. FIG. 1 illustrates the first optical axis 11 of the receiving optical fiber 10 disposed between the second optical axis 21 of the illuminating optical fiber 20 and the reference line 38. Note that the reference line 38 may also be positioned between the first optical axis 11 of the receiving optical fiber 10 and the second optical axis 21 of the illuminating optical fiber 20, with the formula (1) again satisfied.

The third optical axis 31 of the lens 30 may be inclined away from the first optical axis 11 of the receiving optical fiber 10 and the second optical axis 21 of the illuminating optical fiber 20, or may be in parallel with the first optical axis 11 of the receiving optical fiber 10 and the second optical axis 21 of the illuminating optical fiber 20. Whichever the case will be, the formula (1) is satisfied.

If the third optical axis 31 of the lens 30 is inclined away from the first optical axis 11 of the receiving optical fiber 10 and the second optical axis 21 of the illuminating optical fiber 20, the third optical axis 31 and the reference line 38 obliquely cross at the center 35 of the fiber opposing face 34. If the third optical axis 31 of the lens 30 is in parallel with the first optical axis 11 of the receiving optical fiber 10 and the second optical axis 21 of the illuminating optical fiber 20, the third optical axis 31 and the reference line 38 agree.

If the third optical axis 31 of the lens 30 is in parallel with the first optical axis 11 of the receiving optical fiber 10 and the second optical axis 21 of the illuminating optical fiber 20, the third optical axis 31 may agree with the first optical axis 11 of the receiving optical fiber 10, or the third optical axis 31 may shift from the first optical axis 11 of the receiving optical fiber 10. If the third optical axis 31 of the lens 30 agrees with the first optical axis 11 of the receiving optical fiber 10, the distance L1 equals zero.

Since the formula (1) above is satisfied, so that if the third optical axis 31 of the lens 30 is in parallel with the first optical axis 11 of the receiving optical fiber 10 and the second optical axis 21 of the illuminating optical fiber 20 (without consideration on agreement between the third optical axis 31 of the lens 30 and the first optical axis 11 of the receiving optical fiber 10), the focal point 32 of the lens 30 is shifted from the output face 22 of the illuminating optical fiber 20, and the focal point 32 is set in the vicinity of the output face 22.

If the third optical axis 31 of the lens 30 is in parallel with the first optical axis 11 of the receiving optical fiber 10 and the second optical axis 21 of the illuminating optical fiber 20, and the third optical axis 31 of the lens 30 does not agree with the first optical axis 11 of the receiving optical fiber 10, the focal point 32 of the lens 30 is shifted from the input face 12 of the receiving optical fiber 10 and from the output face 22 of the illuminating optical fiber 20, and is set in the vicinity of the input face 12 and the output face 22.

If the third optical axis 31 of the lens 30 agrees with the first optical axis 11 of the receiving optical fiber 10, the focal point 32 of the lens 30 is set on the input face 12 of the receiving optical fiber 10 or in the vicinity thereof.

If the third optical axis 31 of the lens 30 is inclined away from the first optical axis 11 of the receiving optical fiber 10 and from the second optical axis 21 of the illuminating optical fiber 20, the focal point 32 of the lens 30 is set on either one of the input face 12 of the receiving optical fiber 10 and the output face 22 of the illuminating optical fiber 20 or in the vicinity thereof, while being shifted from the other and fallen in the vicinity thereof.

Since the focal point 32 of the lens 30 positioned in this way, the excitation light output from the output face 22 of the illuminating optical fiber 20 is collimated by the lens 30. In other words, the excitation light output from the output face 22 of the illuminating optical fiber 20 is cast, as a near parallel light, onto the site of measurement of the biological tissue. Note that the excitation light as the near parallel light is not always in parallel with the third optical axis 31 of the lens 30.

The fluorescence emitted from the site of measurement of the biological tissue is condensed by the lens 30 onto the input face 12 of the receiving optical fiber 10, and then enters the input face 12.

A mirror may be disposed between the fiber-opposing face 34 of the lens 30, and the input face 12 of the receiving optical fiber 10 and the output face 22 of the illuminating optical fiber 20. In this configuration, the excitation light output from the output face 22 of the illuminating optical fiber 20 is reflected on the mirror, and enters the fiber-opposing face 34 of the lens 30. In addition, the fluorescence emitted from the site of measurement of the biological tissue and cast by the lens 30 is reflected on the mirror, and then enters the input face 12 of the receiving optical fiber 10. While the first optical axis 11 of the receiving optical fiber 10 and the second optical axis 21 of the illuminating optical fiber 20 are bent by the mirror, the relation expressed by the formula (1) above still applies to the portions of the first optical axis 11 and second optical axis 21 which fall on the lens 30 side of the mirror.

Since the relative positional relation among the receiving optical fiber 10, the illuminating optical fiber 20 and the lens 30 is optimized as described above, and in particular, since the formula (1) is satisfied, then the effects (1) to (3) below will arise:

(1) The fluorescence emitted from the site of measurement of the biological tissue efficiently enter the input face 12 of the receiving optical fiber 10. In other words, the receiving optical fiber 10 is suppressed from being lowered in the intensity of fluorescence which is incident thereon.

(2) Noise caused by reflection of light on the fiber-opposing face 34 of the lens 30 and on the object-opposing face 36 may be reduced.

(3) So-called SN ratio may be enhanced, and thereby the noise caused by reflection of light on the fiber-opposing face 34 of the lens 30 or on the object-opposing face 36 may be made less affective.

Figure 2:
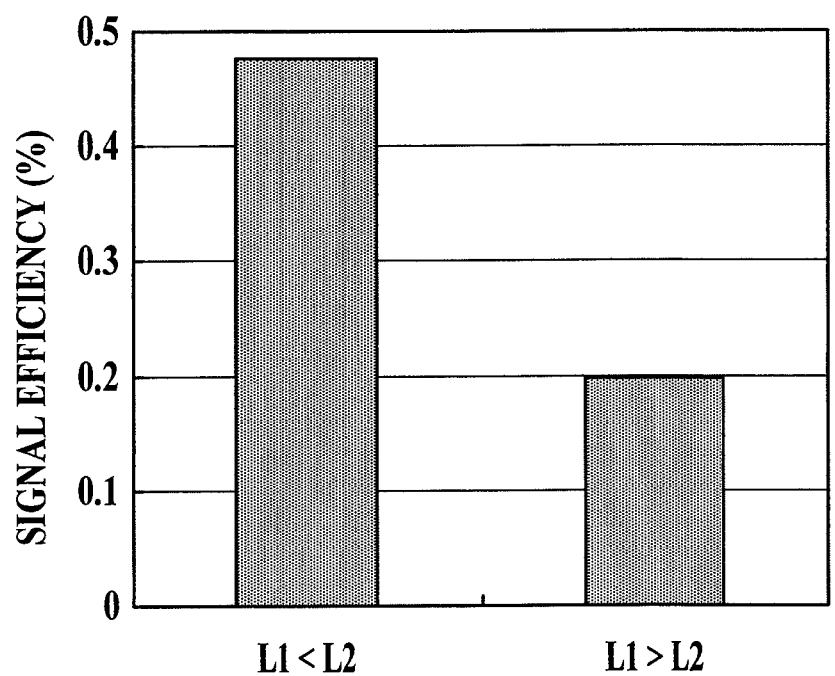
FIG. 2 This is a graph illustrating efficiency of incidence of light into an input face of a receiving optical fiber.

FIG. 2 is a graph illustrating intensity of fluorescence incident on the input face 12 of the receiving optical fiber 10. FIG. 2 shows results of a simulation on the efficiency (ratio) of intensity of fluorescence incident on the input face 12 of the receiving optical fiber 10, while assuming the intensity of fluorescence emitted from the site of measurement of the biological tissue as 100%. As shown in FIG. 2, the efficiency of intensity of the fluorescence incident on the input face 12 of the receiving optical fiber 10 is large so long as the formula (1) above is satisfied, whereas the efficiency of intensity of the fluorescence incident on the input face 12 of the receiving optical fiber 10 is small, when the formula (1) is not satisfied.

Next, an exemplary case where the third optical axis 31 of the lens 30 agrees with the first optical axis 11 of the receiving optical fiber 10 will be detailed (second embodiment). Also an exemplary case where the third optical axis 31 of the lens 30 is in parallel with the first optical axis 11 of the receiving optical fiber 10 and the second optical axis 21 of the illuminating optical fiber 20, and the third optical axis 31 of the lens 30 is shifted from the first optical axis 11 of the receiving optical fiber 10, will be detailed (third embodiment). Also an exemplary case where the third optical axis 31 of the lens 30 is inclined away from the first optical axis 11 of the receiving optical fiber 10 and from the second optical axis 21 of the illuminating optical fiber 20 will be detailed (fourth embodiment).

Second Embodiment

Figure 3A:
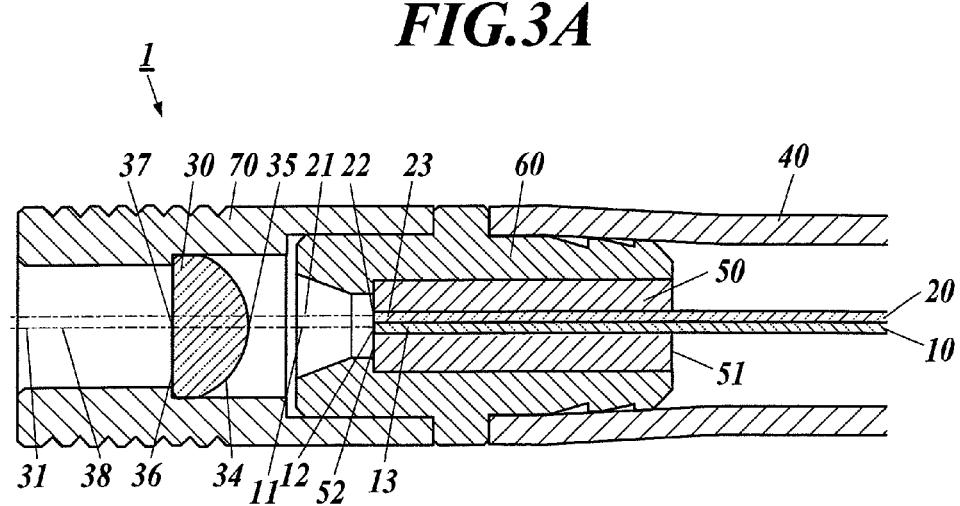
FIG. 3A This is a schematic cross sectional view illustrating a near-end portion of a probe according to a second embodiment of the present invention.
Figure 3B:
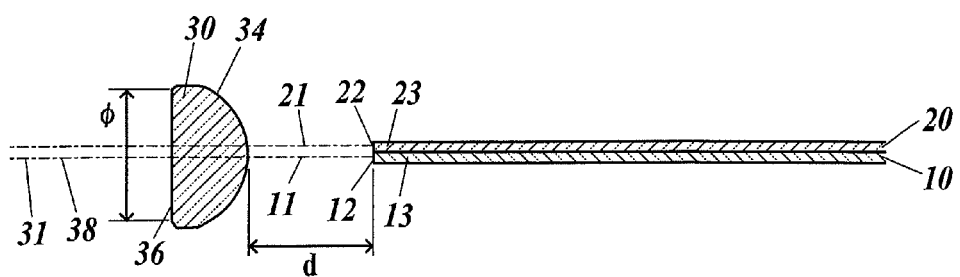
FIG. 3B This is a cross sectional view illustrating the receiving optical fiber, an illuminating optical fiber and the lens illustrated in FIG. 3A, excluding the other constituents.

FIG. 3A is a cross sectional view illustrating a near-end portion of the probe 1, with the third optical axis 31 of the lens 30 agreed with the first optical axis 11 of the receiving optical fiber 10. FIG. 3B is a drawing illustrating only the receiving optical fiber 10, the illuminating optical fiber 20 and the lens 30.

The receiving optical fiber 10 and the illuminating optical fiber 20 are placed so as to extend through a hollow tube 40 from one end to the other end thereof. The tube 40 is flexible.

A hollow lens holder 70 and the tube 40 are joined with a ferrule holder 60. More specifically, a part of the ferrule holder 60 is fitted to an opening at the end of the tube 40, and the other part of the ferrule holder 60 is fitted to an opening at the end of the lens holder 70.

The ferrule holder 60 is provided as a pipe, and has the ferrule 50 fitted thereto. The near-end portion 13 of the receiving optical fiber 10 and the near-end portion 23 of the illuminating optical fiber 20 extend through the ferrule 50 from one end face 51 to the other end face 52, and the input face 12 of the receiving optical fiber 10 and the output face 22 of the illuminating optical fiber 20 expose on the other end face of the ferrule 50.

The near-end portion 13 of the receiving optical fiber 10 and the near-end portion 23 of the illuminating optical fiber 20 are brought into contact. The input face 12 of the receiving optical fiber 10 and the output face 22 of the illuminating optical fiber 20 are aligned. Also the end face of the ferrule 50 is aligned with the input face 12 and the output face 22.

The lens 30 is fixed in the lens holder 70 by the lens holder 70.

The formula (1) above is satisfied, and is therefore the distance L1 equals zero.

Assuming now that the numerical aperture of the illuminating optical fiber 20 at the output face 22 thereof as NA, the effective diameter of the lens 30 as $\phi$, the distance from the center 35 of the fiber opposing face 34 of the lens 30 to the input face 12 of the receiving optical fiber 10 and to the output face 22 of the illuminating optical fiber 20 as d, then the formula (2) below is satisfied:

[Mathematical Formula 3]

$$0 < |L2| \leq \frac{\varphi}{2} - d \times \tan(\sin^{-1} NA). \tag{2}$$

The upper limit of the distance L2 is given by the formula (2). More specifically, the amount of shift ((the distance L2) of the second optical axis 21 of the illuminating optical fiber 20 away from the third optical axis 31 of the lens 30 is limited by characteristics of the lens 30, a positional relation between the lens 30 and the optical fibers 10, 20, and a mode of spreading of light output from the output face 22 of the illuminating optical fiber 20. Conversely, given the distance L2, some limitation will be introduced into the characteristics of the lens 30 and the illuminating optical fiber 20.

By satisfying the formula (2), the excitation light output from the output face 22 of the illuminating optical fiber 20 may be prevented from being partially blocked. In other words, also ray emitted in the direction of maximum angle c ($c=\sin^{-1}$ NA), out of the whole excitation light output from the output face 22, may be incident on the lens 30. Accordingly, the excitation light output from the output face 22 of the illuminating optical fiber 20 may be used in an efficient manner.

Third Embodiment

Figure 4A:
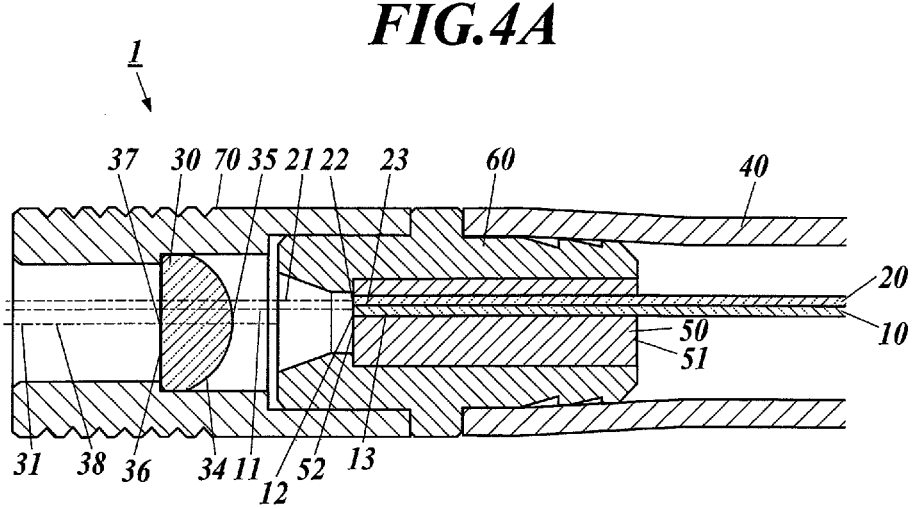
FIG. 4A This is a schematic cross sectional view illustrating a near-end portion of a probe according to a third embodiment of the present invention.
Figure 4B:
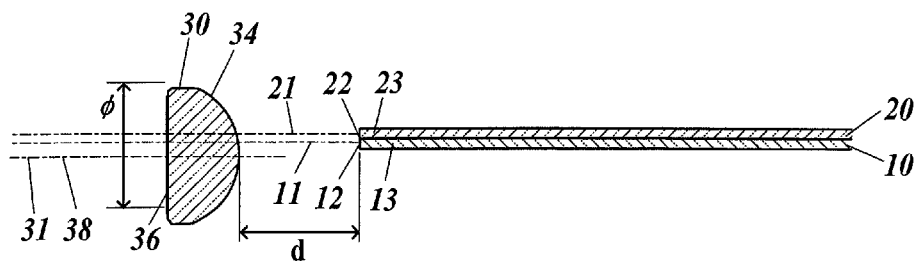
FIG. 4B This is a cross sectional view illustrating the receiving optical fiber, the illuminating optical fiber and the lens illustrated in FIG. 4A, excluding the other constituents.

FIG. 4A is a sectional view illustrating the near-end portion of the probe 1, with the third optical axis 31 of the lens 30 aligned in parallel with the first optical axis 11 of the receiving optical fiber 10 and the second optical axis 21 of the illuminating optical fiber 20, and the third optical axis 31 of the lens 30 is shifted from the first optical axis 11 of the receiving optical fiber 10. FIG. 4B illustrates only the receiving optical fiber 10, the illuminating optical fiber 20 and the lens 30.

The tube 40, the ferrule 50, the ferrule holder 60 and the lens holder 70 will not be explained herein, since they are same as those described in Second Embodiment.

The near-end portion 13 of the receiving optical fiber 10 and the near-end portion 23 of the illuminating optical fiber 20 are immobilized by the ferrule 50, and the near-end portions 13, 23 are brought into contact with each other. The input face 12 of the receiving optical fiber 10 and the output face 22 of the illuminating optical fiber 20 are aligned.

The formula (1) above is satisfied. The first optical axis 11 of the receiving optical fiber 10 is placed between the second optical axis 21 of the illuminating optical fiber 20 and the third optical axis 31 of the lens 30.

The formula (2) above is satisfied, and thereby the upper limit of the distance L2 is determined. Accordingly, the excitation light output from the output face 22 of the illuminating optical fiber 20 may be prevented from being partially blocked.

Fourth Embodiment

Figure 5A:
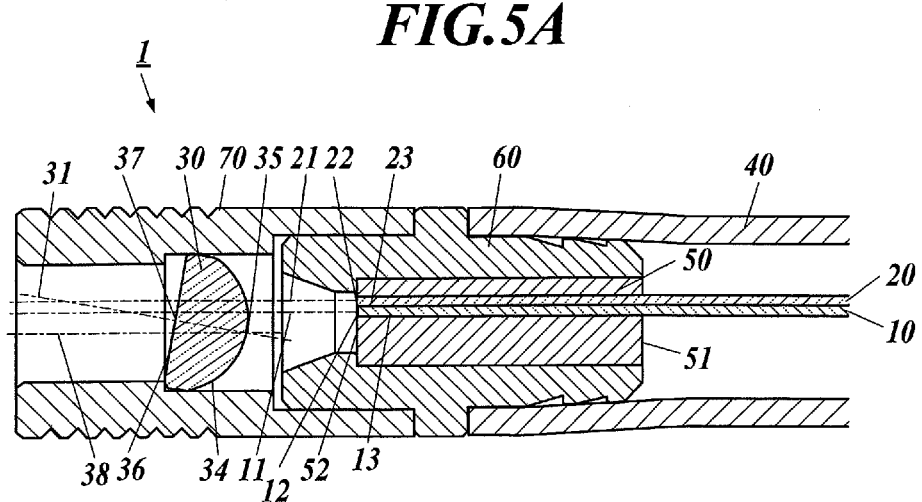
FIG. 5A This is a schematic cross sectional view illustrating a near-end portion of a probe according to a fourth embodiment of the present invention.
Figure 5B:
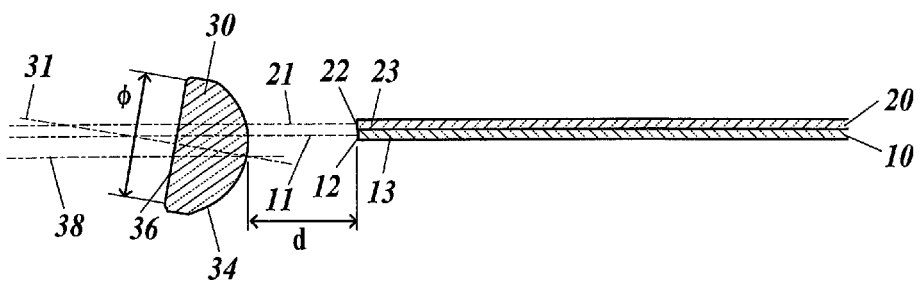
FIG. 5B This is a cross sectional view illustrating the receiving optical fiber, the illuminating optical fiber and the lens illustrated in FIG. 5A, excluding the other constituents.

FIG. 5A is a cross sectional view illustrating the near-end portion of the probe 1, with the third optical axis 31 of the lens 30 inclined away from the first optical axis 11 of the receiving optical fiber 10 and from the second optical axis 21 of the illuminating optical fiber 20. FIG. 5B illustrates only the receiving optical fiber 10, the illuminating optical fiber 20 and the lens 30.

The tube 40, the ferrule 50, the ferrule holder 60 and the lens holder 70 will not be explained herein, since they are same as those described in Second Embodiment.

The third optical axis 31 of the lens 30 immobilized by the lens holder 70 crosses the first optical axis 11 of the receiving optical fiber 10 at an oblique angle. The third optical axis 31 of the lens 30 also crosses the second optical axis 21 of the illuminating optical fiber 20 at an oblique angle.

The formula (1) above is satisfied. The first optical axis 11 of the receiving optical fiber 10 is disposed between the second optical axis 21 of the illuminating optical fiber 20 and the reference line 38.

Assuming now the angle of inclination of the third optical axis 31 of the lens 30 away from the first optical axis 11 of the receiving optical fiber 10 as θ, the numerical aperture of the illuminating optical fiber 20 at the output face 22 thereof as NA, the effective diameter of the lens 30 as φ, and the distance from the center 35 of the fiber opposing face 34 of the lens 30 to the input face 12 of the receiving optical fiber 10 and to the output face 22 of the illuminating optical fiber 20 as d, then the formula (3) below is satisfied.

[Mathematical Formula 4]

$$0 < |L2| \leq (\sin\theta + \cos\theta)\frac{\varphi}{2} - d \times \tan(\sin^{-1} NA) \qquad (3)$$

The upper limit of the distance L2 is determined by the formula (3). By satisfying the formula (3), the excitation light output from the output face 22 of the illuminating optical fiber 20 may be prevented from being partially blocked.

Example 1

A configuration having the third optical axis 31 of the lens 30 aligned in agreement with the first optical axis 11 of the receiving optical fiber 10 (see FIG. 3A) was simulated.

Conditions of the simulation are as follow:
φ=1.36 mm
f=1.125 mm
R=0.68 mm
NA=0.22
NA2=0.22
D=1.7 mm
r1=0.1 mm
r2=0.1 mm
L2=0.11 mm Where, φ is the effective diameter of the lens 30, f is focal length of the lens 30, R is the radius of the lens 30, NA is the numerical aperture of the illuminating optical fiber 20 at the output face 22 thereof, NA2 is the numerical aperture of the receiving optical fiber 10 at the input face 12 thereof, D is the distance from the lens 30 to a target (object which emits fluorescence), r1 is the diameter of the core of the illuminating optical fiber 20, r2 is the diameter of the core of the receiving optical fiber 10, L2 is the distance from the center 35 of the fiber opposing face 34 to the second optical axis 21 of the illuminating optical fiber 20 (the same will apply also to Example 2 and Example 3 described later).

Intensity of scattered light which enters the input face 12 of the receiving optical fiber 10 was determined by the simulation, while varying the distance d from the center 35 of the fiber opposing face 34 to the input face 12 of the receiving optical fiber 10. Also intensity of noise caused by reflection of scattered light on the fiber-opposing face 34 of the lens 30, the object-opposing face 36 and so forth was determined by the simulation. Also SN ratio was determined by the simulation. Since the fluorescence is supposed to randomly propagate just like scattered light, so that the scattered light at the site of measurement, in place of the fluorescence at the site of measurement, was simulated.

Figure 6:
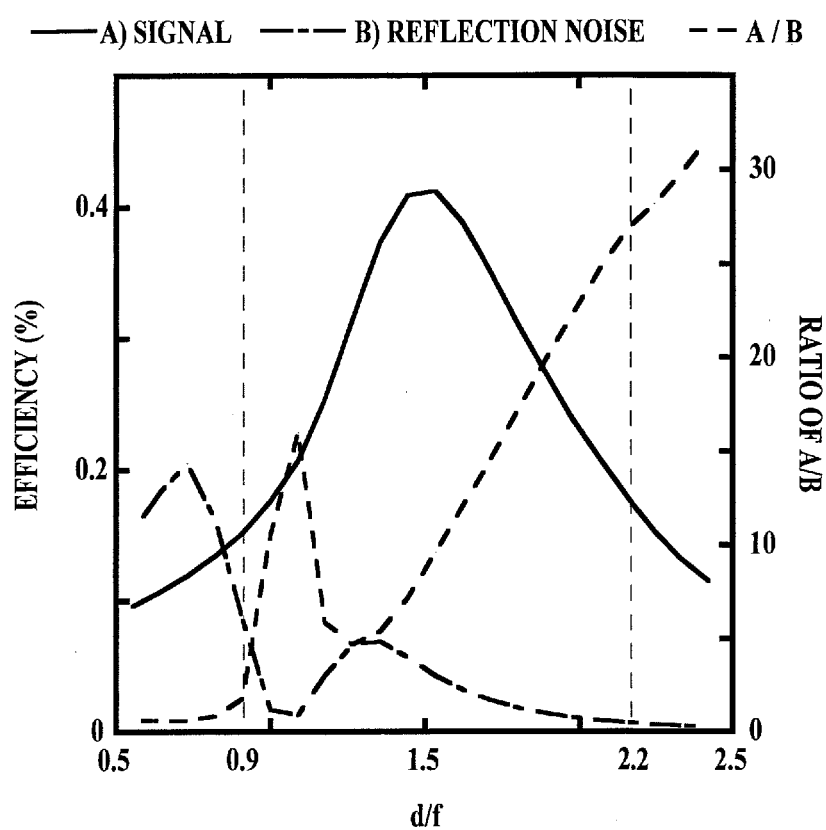
FIG. 6 This is a graph illustrating efficiency of incidence of light, efficiency of reflection noise and SN ratio in the probe illustrated in FIG. 3A.

Results of the simulation are shown in FIG. 6. Explanatory note "A) Signal" in the drawing represents the ratio of intensity of scattered light (efficiency) incident on the input face 12 of the receiving optical fiber 10, assuming the intensity of light output from the illuminating optical fiber 20 as 100%. Explanatory note "B) Reflection noise" in the drawing represents ratio of intensity of scattered light (efficiency) not incident on the input face 12 of the receiving optical fiber 10, due to reflection on the fiber-opposing face 34 of the lens 30, the object-opposing face 36 and so forth, assuming the intensity of light output from the illuminating optical fiber 20 as 100%. Explanatory note "A/B" in the drawing represents SN ratio.

By substituting L2=0.11 into the formula (2), obtained are d≤2.5 and d/f≤2.2.

In this way, the upper limit of the distance d from the center 35 of the fiber opposing face 34 to the input face 12 of the receiving optical fiber 10 is determined. It is understood from the graph in FIG. 6 that, in the range expressed by d/f≤2.2, the light emitted from the target efficiently enters the input face 12 of the receiving optical fiber 10 (see explanatory note "A) Signal"). It is also understood that the reflection noise is low, and the SN ratio is high (see explanatory note "B) Reflection Noise", and explanatory note "A/B").

A maximum SN ratio in the range of d/f≤2.2 appears at d/f=2.2, and the SN ratio at d/f=0.9 is one tenth of the SN ratio at d/f=2.2. The range of 0.9<d/f≤2.20 is found to be optimum for achieving sufficiently small noise and high efficiency.

In the configuration of this Example, the noise level is less readily reduced, and the SN ratio is less readily elevated even if the distance between the optical fibers 10, and the lens 30 is increased, since the region of reflection on the lens 30 causative of noise is large. The d/f is therefore considered to range from a distance slightly shorter than the focal length f up to the upper limit determined by the distance L2.

Example 2

A configuration having the third optical axis 31 of the lens 30 aligned in parallel with the first optical axis 11 of the receiving optical fiber 10 and with the second optical axis 21 of the illuminating optical fiber 20, and having the third optical axis 31 of the lens 30 shifted from the first optical axis 11 of the receiving optical fiber 10 (see FIG. 4A), was simulated.

Figure 7:
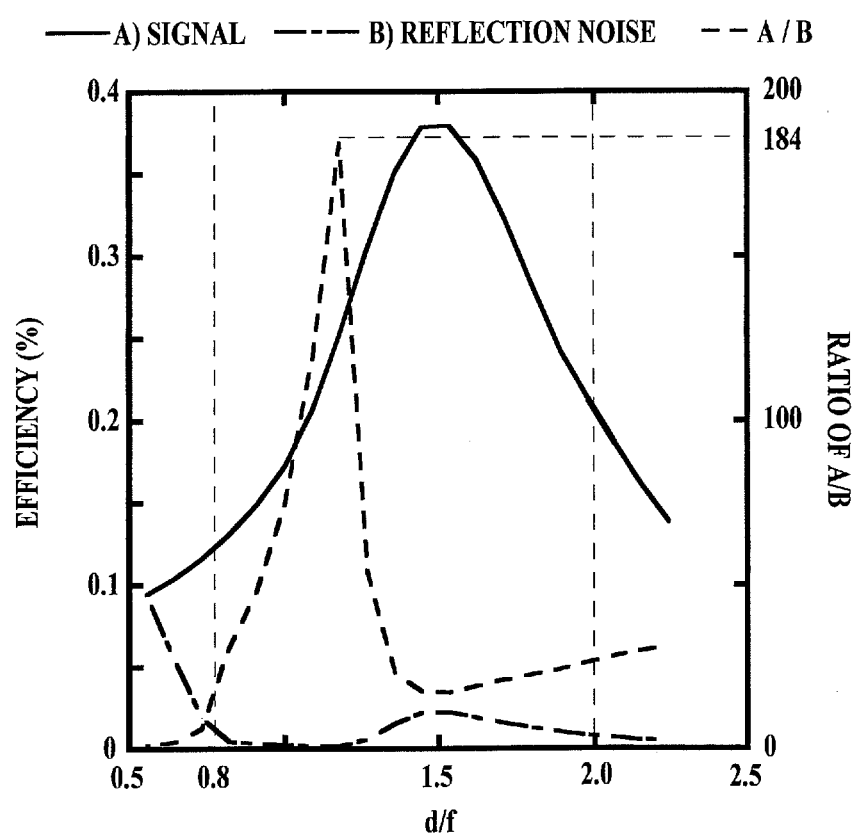
FIG. 7 This is a graph illustrating efficiency of incidence of light, efficiency of reflection noise and SN ratio in the probe illustrated in FIG. 4A.

Conditions of the simulation are as follow.
φ=1.36 mm
f=1.125 mm
R=0.68 mm
NA=0.22
NA2=0.22
D=1.7 mm
r1=0.1 mm
r2=0.1 mm
L2=0.15 mm Results of the simulation are shown in FIG. 7. Explanatory notes in FIG. 7 are same as those in FIG. 6.

By substituting L2=0.15 into the formula (2), obtained are d≤2.3 and d/f≤2.0.

In this way, the upper limit of the distance d from the center 35 of the fiber opposing face 34 to the input face 12 of the receiving optical fiber 10 is determined. It is understood from the graph in FIG. 7 that, in the range expressed by d/f≤2.0, the light emitted from the target efficiently enters the input face 12 of the receiving optical fiber 10, thereby ensuring sufficiently low noise and high SN ratio.

The SN ratio at d/f=0.8 is one tenth of the maximum SN ratio (=184) in the range of d/f≤2.0. The range of 0.8<d/f≤2.0 is found to be optimum for achieving sufficiently small noise and high efficiency.

Example 3

A configuration having the third optical axis 31 of the lens 30 inclined away from the first optical axis 11 of the receiving optical fiber 10 and from the second optical axis 21 of the illuminating optical fiber 20 (see FIG. 5A) was simulated.

Conditions of the simulation are as follow.
φ=1.36 mm
f=1.125 mm
R=0.68 mm
NA=0.22
NA2=0.22
D=1.7 mm
r1=0.1 mm
r2=0.1 mm
L2=0.25 mm
θ=5°

Note that θ represents the angle of inclination of the third optical axis 31 of the lens 30 away from the first optical axis 11, the second optical axis 21 and the reference line 38.

Results of the simulation are shown in FIG. 8. Explanatory notes in FIG. 8 are same as those in FIG. 6.

By substituting L2=0.25 into the formula (3), obtained are d≤2.1 and d/f≤1.9. In this way, the upper limit of the distance d from the center 35 of the fiber-opposing face 34 to the input face 12 of the receiving optical fiber 10 is determined. It is understood from the graph in FIG. 8 that, in the range expressed by d/f≤1.9, the light emitted from the target efficiently enters the input face 12 of the receiving optical fiber 10, thereby ensuring sufficiently low noise and high SN ratio.

The SN ratio at d/f=1.0 is one tenth of the maximum SN ratio in the range of d/f≤1.9. The range of 1.0<d/f≤1.9 is found to be optimum for achieving sufficiently small noise and high efficiency.

In this Example, the noise may be reduced by inclining the lens 30 so as to divert the reflection on the lens 30. The lower limit of the distance d from the center 35 of the fiber opposing face 34 to the input face 12 of the receiving optical fiber 10 is given by the focal length f or around, whereas the upper limit of the distance d is given by the formula (3).

As described in Example 1 to Example 3, the efficiency of reception of light, the reflection noise on the lens 30, and the ratio of them were determined by the simulation. It was confirmed by the simulation that the reflection noise on the lens 30 may be reduced by shifting the second optical axis 21 of the illuminating optical fiber 20 from the reference line 38 or from the third optical axis 31 of the lens 30, or by inclining the lens 30.

However, the distance L1 from the center 35 of the fiber opposing face 34 to the first optical axis 11 of the receiving optical fiber 10, the distance L2 from the center 35 of the fiber opposing face 34 to the second optical axis 21 of the illuminating optical fiber 20, and the angle of inclination θ of the lens 30 are limited by geometry of the lens 30, divergence of the excitation light output from the output face 22 of the illuminating optical fiber 20 (numerical aperture NA), and the distance d between the lens 30 and the optical fibers 10, 20. This fact was demonstrated by the formula (2) and formula (3).

Considering the above, it was shown that the lower limit of the distance d from the lens 30 and the optical fibers 10, is given by the focal length f or around of the lens 30, whereas the upper limit of the distance d is given by the limit value restricted by the distance L1, the distance L2 and the angle of inclination θ.

INDUSTRIAL APPLICABILITY

The present invention is applicable to a probe configured to illuminate the site of measurement of the biological tissue with light, and to receive light emitted from the site of measurement.

EXPLANATION OF SYMBOLS 1 probe
10 receiving optical fiber
11 first optical axis
12 input face
20 illuminating optical fiber
21 second optical axis
22 output face
30 lens
31 third optical axis
34 fiber-opposing face
35 center
36 object-opposing face (flat surface)

The invention claimed is:

1. A probe comprising:
a receiving optical fiber having a first optical axis and having at an end thereof an input face orthogonal to the first optical axis;
an illuminating optical fiber having a second optical axis parallel to the first optical axis and having at an end thereof an output face orthogonal to the second optical axis; and
a lens having a positive power, which is configured to cast light output from the output face of the illuminating optical fiber onto a site of measurement of a biological tissue, and is configured to condense light emitted from the site of measurement of the biological tissue onto the input face of the receiving optical fiber,
wherein the lens includes a convex surface faced to the input face and the output face, a flat surface formed opposite to the convex surface, and a third optical axis which crosses the convex surface at a center thereof and orthogonally crosses the flat surface at a center thereof,
wherein a distance, if any, along a direction from the center of the convex surface to the first optical axis and perpendicular to the first optical axis is shorter than a distance along a direction from the center of the convex surface to the second optical axis and perpendicular to the second optical axis, and
wherein the first optical axis, the second optical axis and the third optical axis are parallel to each other.

2. The probe of claim 1, wherein, assuming a numerical aperture of the output face of the illuminating optical fiber as NA, an effective diameter of the lens as $\phi$, a distance from the center of the convex surface of the lens to the input face of the receiving optical fiber and to the output face of the illuminating optical fiber as d, and a distance along a direction from the center of the convex surface to the second optical axis and perpendicular to the second optical axis as L2, the following relation is satisfied:

$$0 < |L2| \leq \frac{\varphi}{2} - d \times \tan(\sin^{-1} NA).$$

3. The probe of claim 2, wherein the third optical axis and the first optical axis are collinear.

4. The probe of claim 1, wherein the third optical axis and the first optical axis are collinear.

5. A probe comprising:
a receiving optical fiber having a first optical axis and having at an end thereof an input face orthogonal to the first optical axis;
an illuminating optical fiber having a second optical axis parallel to the first optical axis and having at an end thereof an output face orthogonal to the second optical axis; and
a lens having a positive power, which is configured to cast light output from the output face of the illuminating optical fiber onto a site of measurement of a biological tissue, and is configured to condense light emitted from the site of measurement of the biological tissue onto the input face of the receiving optical fiber,
wherein the lens includes a convex surface faced to the input face and the output face, a flat surface formed opposite to the convex surface, and a third optical axis which crosses the convex surface at a center thereof and orthogonally crosses the flat surface at a center thereof,
wherein a distance, if any, along a direction from the center of the convex surface to the first optical axis and perpendicular to the first optical axis is shorter than a distance along a direction from the center of the convex surface to the second optical axis and perpendicular to the second optical axis,
wherein the third optical axis is inclined away from the first optical axis, and
wherein, assuming an angle of inclination of the third optical axis away from the first optical axis as $\theta$, the numerical aperture of the output face of the illuminating optical fiber as NA, the effective diameter of the lens as $\phi$, a distance from the center of the convex surface of the lens to the input face of the receiving optical fiber and the output face of the illuminating optical fiber as d, and a distance along a direction from the center of the convex surface to the second optical axis and perpendicular to the second optical axis as L2, the following relation is satisfied:

$$0 < |L2| \leq (\sin\theta + \cos\theta)\frac{\varphi}{2} - d \times \tan(\sin^{-1} NA).$$

* * * * *